US006196969B1

United States Patent
Bester et al.

(10) Patent No.: US 6,196,969 B1
(45) Date of Patent: Mar. 6, 2001

(54) TISSUE RETRACTOR ADAPTED FOR THE ATTACHMENT OF AN AUXILIARY ELEMENT

(75) Inventors: Leon W. Bester, Belmont; David A. Walsh, Somerville, both of MA (US)

(73) Assignee: Lab Engineering & Manufacturing, Inc., North Billerica, MA (US)

( * ) Notice: Subject to any disclaimer, the term of this patent is extended or adjusted under 35 U.S.C. 154(b) by 0 days.

(21) Appl. No.: 09/316,231

(22) Filed: May 21, 1999

(51) Int. Cl.[7] ............................................. A61B 1/32
(52) U.S. Cl. ............................................. 600/224; 600/219
(58) Field of Search .................................. 600/201, 219, 600/224, 220, 221, 213, 214, 210

(56) References Cited

U.S. PATENT DOCUMENTS

| D. 378,780 | 4/1997 | Shuler .................. D24/146 |
| 569,839 | 10/1896 | Roeloffs . |
| 579,625 | * 3/1897 | Willbrandt .................. 600/224 |
| 1,094,575 | * 4/1914 | Joutras .................. 600/224 |
| 1,194,319 | * 8/1916 | Pretts .................. 600/224 |
| 1,499,186 | 6/1924 | Murphy . |
| 3,038,467 | 6/1962 | Sovatkin . |
| 3,470,872 | 10/1969 | Grieshaber . |
| 3,747,592 | 7/1973 | Santos . |
| 3,998,217 | 12/1976 | Trumbull . |
| 4,034,746 | 7/1977 | Williams . |
| 4,754,746 | 7/1988 | Cox . |
| 4,896,661 | 1/1990 | Begert et al. .................. 606/86 |
| 5,297,538 | 3/1994 | Daniel . |
| 5,350,383 | 9/1994 | Schmieding et al. .................. 606/96 |
| 5,618,308 | 4/1997 | Holmes et al. .................. 606/205 |
| 5,681,333 | 10/1997 | Burkhart et al. .................. 606/148 |
| 5,685,826 | 11/1997 | Bonutti .................. 600/204 |
| 5,785,647 | 7/1998 | Tompkins et al. .................. 600/201 |
| 5,810,721 | 9/1998 | Mueller et al. .................. 600/206 |
| 5,931,777 | * 8/1999 | Sava .................. 600/219 X |

FOREIGN PATENT DOCUMENTS

| 4425652 | 1/1996 | (DE) . |
| 9827869 | 7/1998 | (WO) . |

OTHER PUBLICATIONS

"A Retractor For Cholecystectomy", The Lancet, Oct. 22, 1955, p. 854.*

* cited by examiner

Primary Examiner—Jeffrey A. Smith
(74) Attorney, Agent, or Firm—George A. Herbster; Pearson & Pearson (57) ABSTRACT

A tissue retractor with an adjustable center claw. The retractor includes two pivoted retractor arms. An axially and angularly displaceable, spring biased clamping mechanism is positioned on the pivot axis. In a mounting position, a elongated clamping element aligns with a slot in the center claw. When the center claw is positioned and the clamp moves to its clamping position, the elongated clamping member clamps the center claw in position. The counter-facing surfaces of the center claw and the clamping member are toothed to provide a positive one-way ratchet clamp.

20 Claims, 6 Drawing Sheets

TISSUE RETRACTOR ADAPTED FOR THE ATTACHMENT OF AN AUXILIARY ELEMENT

BACKGROUND OF THE INVENTION

1. Field of the Invention

This invention generally relates to surgical instruments and more specifically to tissue retractors for use in various surgical procedures.

2. Description of Related Art

Surgical retractors are well known in the medical arts, particularly retractors that separate body tissue to enable a surgeon access to an operating site. Generally these retractors include two arms that can pivot about an axis at an intermediate position to form a scissors-like mechanism. Squeezing finger grips at one end of each arm causes a pair of retractor claws at the other ends of each arm to separate. Once the desired tissue separation is achieved, a ratchet sector on one arm and a pawl on the other arm lock the arms in place relative to each other and thereby maintain the tissue separation. The following patents disclose some examples of such retractors:

U.S. Pat. No. 3,038,467 (1962) Sovatkin
U.S. Pat. No. 3,470,872 (1969) Grieshaber These retractors, however, only provide separation at two opposed locations. The following patent:

U.S. Pat. No. 3,998,217 (1976) Trumbull et al. discloses another type of retractor device that engages tissue at four different positions. While such an approach provides more tissue contacts, it has not gained wide acceptance. Scissors-type retractors continue to be the instruments of choice.

There has also been introduced a variation on a scissors-type retractor whereby a central claw attaches to the retractor to provide three tissue contacts. Specifically, one retractor with this capability includes two retractor arms that can pivot about a pivot axis. Each arm includes a finger grip and a claw at opposite ends. A central claw has an intermediate planar portion with a clearance passage at an intermediate location along an elongated slot. A wing bolt attaches to a threaded receptacle formed in one of the arms along the pivot axis. To attach the central claw, a surgeon grasps the retractor in one hand and uses the other hand to loosen the wing bolt. Then the surgeon aligns the clearance passage with the wing bolt so that the central claw passes over the wing bolt. The surgeon must then displace the central claw so that a flange on the wing bolt overlies portions of the central claw to capture it. Next the surgeon positions the central claw against a patient's tissue and then tightens the wing bolt to effect clamping solely by generating frictional forces between smooth facing surfaces of the wing bolt flange and the central claw.

This arrangement does advantageously increase the number of tissue contact points. However, if it becomes necessary to reset the position of the central claw, the surgeon must use both hands to hold the retractor in position, loosen the wing bolt, move the central claw and then hold the central claw in position while tightening the wing bolt. In addition, the clearance passage through the central claw limits the range of longitudinal motion of the central claw. As will be apparent, it will not be possible to move the central claw to a position at which the clearance passage aligns with the wing bolt. If such an alignment occurs, the central claw will detach from the retractor. Moreover, the central claw clamps to one of the arms thereby fixing the angular position of the central claw relative to that arm. If the surgeon adjusts the arm separation, the central claw will move with that arm in a fixed angular relationship. Consequently, the central arm will not be equiangularly spaced from the two arms without repositioning the central claw as described above. What is needed is a scissors-type retractor that a surgeon can operate with one hand even when attaching or manipulating a central claw and that maintains equiangular spacing between the central claw and the retractor arms even as the surgeon changes the separation of the retractor arms.

SUMMARY

Therefore, it is an object of this invention to provide a tissue retractor with the ability to attach a central claw in a simple one-handed operation.

Another object of this invention is to provide a tissue retractor with a central claw that is readily adjustable position-wise in a simple one-handed operation.

Still another object of this invention is to provide a tissue retractor in which a central claw remains centered during adjustment of the retractor arms.

In accordance with one aspect of this invention, a tissue retractor includes first and second arms connected to rotate about a pivot axis. Each arm includes a retractor claw at one end. A clamp on the pivot axis mounts to the first and second arms for adjustment between first and second positions. The clamp, in its first position, enables the auxiliary element to be positioned relative to said pivot. In a second position, the clamp produces positive interference to relative motion between the clamp and the auxiliary element.

In accordance with another aspect of this invention a tissue retractor comprises first and second arms connected to rotate about a pivot axis, each arm including a retractor claw at one end thereof for engaging tissue. An auxiliary claw has an elongated intermediate body portion with an elongated slot therethrough. A central actuator extends through the first and second arms along the pivot axis, and an elongated clamping member attaches to an end of the central actuator. The central actuator and clamping member are movable axially and angularly relative to the first and second arms between a mounting end position and a clamping end position. The clamping member is aligned with the elongated slot in the auxiliary claw in the mounting end position and is transverse to the elongated slot in the clamping end position.

In accordance with still another aspect of this invention, a tissue retractor comprises first and second retractor arms each having a grip at a first end and interfitting intermediate portions that define a pivot axis. A hinged, replaceable claw mechanism is located at the second end of each arm. A flanged sleeve mounts through the interfitting intermediate portions in a first direction along the pivot axis whereby the first and second retractor arms can rotate about the sleeve. A centering body has a portion extending into the sleeve in the first direction and can be rotated with respect to the sleeve and first and second retractor arms. The centering body also has elongated planar support surfaces formed parallel to the flange on the sleeve on opposite sides of the pivot axis. Centering springs between the centering body and each of the first and second retractor arms center the centering body angularly with the elongated planar support surface lying along an axis intermediate axes through each of the retractor arms. A spring biased actuator with a transverse portion and a body portion extends through the sleeve and centering body portion in a second direction along the pivot axis. An elongated clamp attaches to the actuator body portion from the other direction so the transverse portion and the clamp are positioned on opposite sides of the interfitting, intermediate portions of the retractor arms with the actuator and clamp being angularly and axially displaceable between a mounting end position when the clamp is positioned on the support surfaces and a clamping end position when the clamp is rotated to be transverse to the support surfaces. With this structure a center claw having an intermediate portion with an elongated slot and a toothed surface, a claw and a handle portion extending from the opposite ends of the intermediate portion can be easily attached when the clamp is in the mounting end position. In an intermediate position of the clamp the center claw can move in either direction with respect while remaining captured to the retractor. In the clamping end position the clamp and toothed portions of the center claw provide a one-way ratchet to limit motion of the central claw toward the handle portions of the first and second arms.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
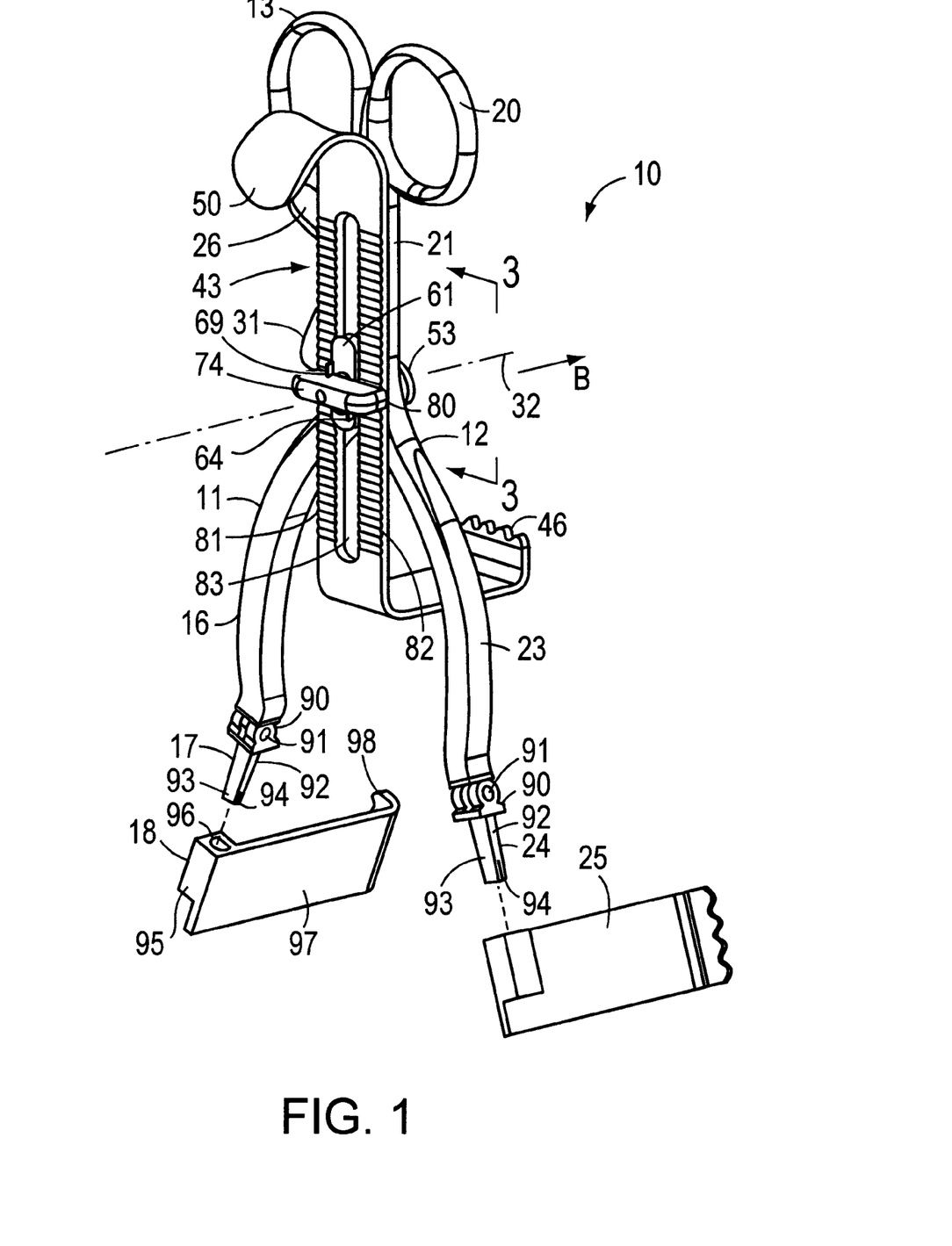
FIG. 1 is a perspective view of a retractor and central claw constructed in accordance with this invention.

FIG. 1 depicts a soft tissue retractor 10 that incorporates this invention. The basic structure of the retractor 10 comprises a first arm 11 and second arm 12 that are adapted to rotate about a pivot axis.

Figure 2:
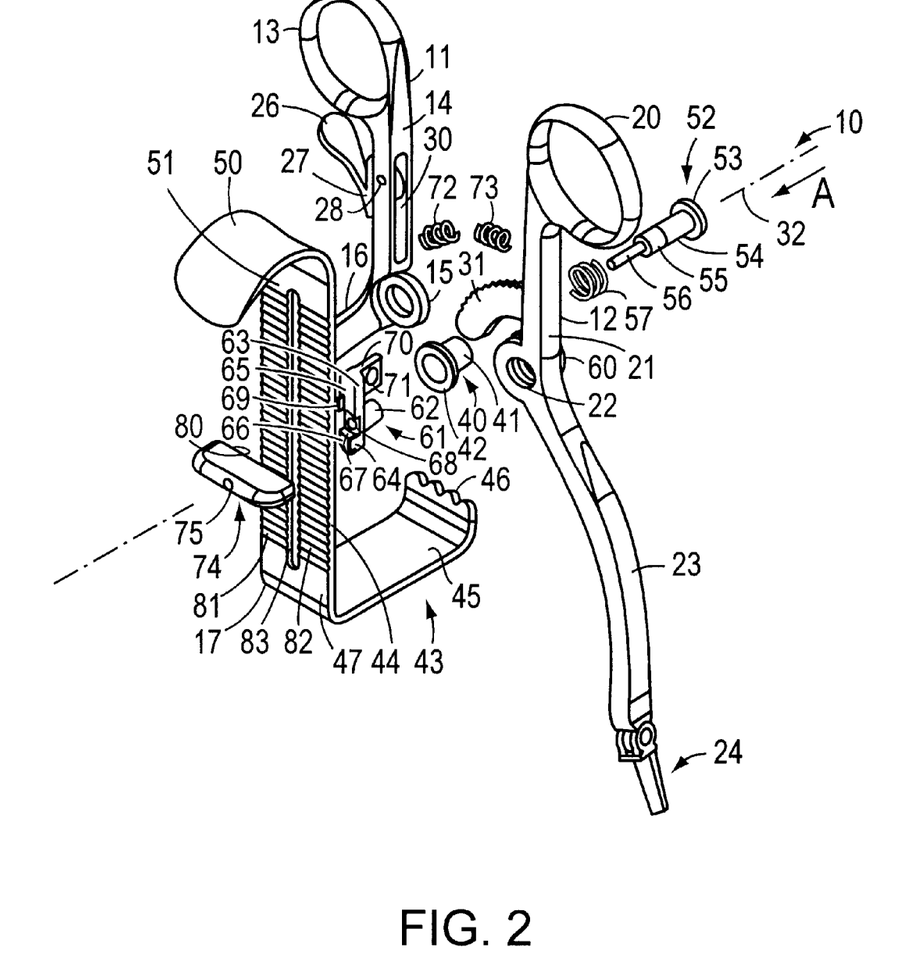
FIG. 2 is an exploded perspective view of a portion of the retractor and central claw shown in FIG. 1.

Looking first at arm 11 as depicted in FIGS. 1 and 2, a finger grip 13 at a first end provides a grip for a surgeon. An upper portion 14 extends between the finger grip 13 and an intermediate portion constituted by a flat member 15 having a generally annular form. A lower portion 16 extends from the intermediate portion 15 to a hinged claw coupler 17 that receives a claw 18. Likewise the second arm 12 includes a finger grip 20, an upper portion 21, an intermediate portion 22, a lower portion 23 and a hinged claw coupler 24 that also receives a claw 25, like the claw 18. In this case, however, the intermediate portion 22 is formed by two annular members spaced by an amount corresponding to the thickness of the intermediate portion 15.

As particularly shown in FIG. 2, the first arm 11 additionally includes a thumb actuator 26 that moves a pawl 27 about a pivot 28. The pawl 27 aligns with a slot 30 through the upper arm portion 14 to receive a ratchet sector 31 attached to the upper portion 21 of the arm 12.

During assembly of the parts shown in FIG. 2 into the assembled form shown in FIG. 1, the intermediate portions 15 and 22 are joined to define a pivot axis 32 for the arms 11 and 12. The ratchet sector 31 then extends through the slot 30 to be engaged by the pawl 27 thereby to allow the surgeon to operate the finger grips 13 and 20 until an appropriate displacement has been obtained. The pawl 27 and ratchet sector 31 then maintain that separation as known in the art. In a preferred form, the pawl 27 and ratchet sector 31 prevent closure of the claws while allowing the surgeon to increase the separation without any need to manipulate the thumb actuator.

The mechanism that defines the pivot axis 32 and enables the arms 11 and 12 to pivot relative to each other includes a flanged sleeve 40 with a cylindrical body portion 41 and a flange 42. The cylindrical body portion is positioned through the central apertures of the interfitted intermediate portions 15 and 22. This allows each of the arms 11 and 12 to rotate relative to each other and relative to the sleeve 40.

FIGS. 1 and 2 also disclose an auxiliary element in the specific form of a central claw 43 that includes a planar intermediate portion 44 with a claw offset 45 terminating in a claw 46 spaced from the intermediate portion 44. The claw offset 45 extends from one end 47 of the intermediate portion. A u-shaped finger grip 50 extends from the other end 51 of the intermediate portion 44. In this embodiment, the claw 46 and finger grip 50 lie on opposite sides of a plane through the intermediate portion 44.

FIGS. 1 and 2 further depict a clamping mechanism that permits the ready use of the center claw 43. A first element of this mechanism is an actuator 52 that extends along the pivot axis 32 and is inserted through the sleeve 40 from a first direction, namely from the right in FIG. 2 as depicted by an arrow A. The actuator 52 includes a flange or head 53 and axially positioned body portions 54, 55 and 56 of successively decreasing diameters extending in seriatim from the head 53 along the pivot axis 32. The largest diameter body portion 54 is coaxial with a compression spring 57 that acts on the head 53 and the intermediate portion 22 of the arm 12 by being seated in a recess 58 form in a boss 60 that is on the arm 12 and that is coaxial with the pivot axis 32, as more clearly shown in FIG. 3.

Figure 3:
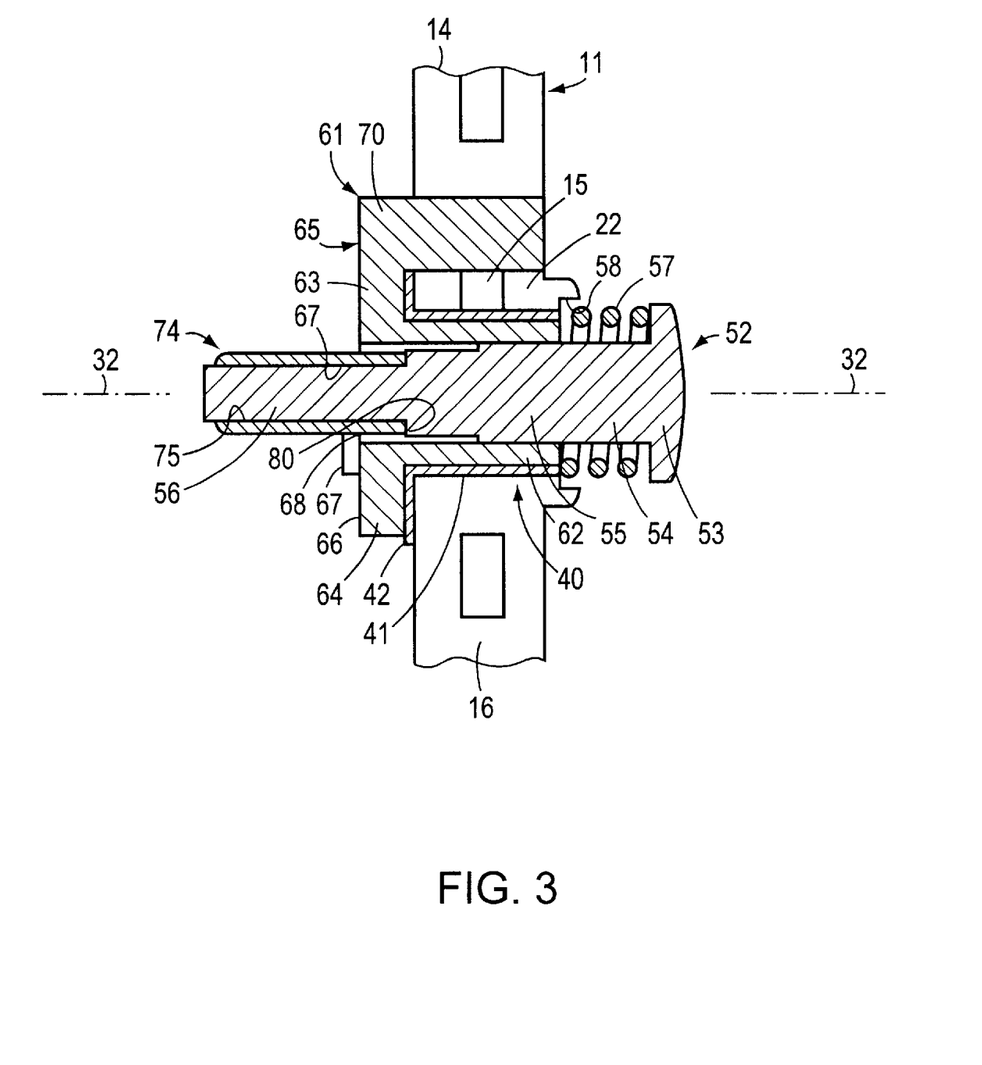
FIG. 3 is a cross section of the clamping mechanism taken along lines 3—3 in FIG. 1.

The next clamping mechanism element, a centering element 61, has a cylindrical body portion 62 extending along the pivot axis 32 as most clearly shown in FIGS. 2 and 3. Two oppositely extending radial members 63 and 64 form transverse support surfaces 65 and 66 respectively on the side of the element 61 opposite the body portion 62. A transverse cavity 67 is formed between the radial members 63 and 64. A central passage 68 extends through the cylindrical portion 62 and exits at the cavity 67. Tabs 69 extend from the surfaces 65 and 66 to form limits or stops for angular displacement of the actuator 52 as described later.

An axially extending arm 70 from the radial body portion 63 parallels the pivot axis 32 and extends toward the head 53 of the actuator 52; that is, to the right in FIG. 2. Spring support wells are located on each side of this arm 70, with only one such well 71 being shown in FIG. 2. This well receives a spring 73 that is captured in a well, not shown, in the arm just above the intermediate portion 22. A similar well, formed internally of the slot 30 in the arm 11 just above the intermediate portion 15, captures another spring 72.

The springs 72 and 73 are matched in a preferred embodiment of this invention. Consequently as the separation of the arms 11 and 12 changes, the springs 72 and 73 maintain the arm 71 at a middle position between the arms 11 and 12. This assures that the element 61 will position the body portions 63 and 64 along an axis that bifurcates axes through the arms 11 and 12.

During assembly, the cylindrical body 62 is positioned in the sleeve 40. Then the actuator 52, with the spring 57, is inserted through the sleeve 40 and the passage through the cylindrical body 62 in the direction of the arrow A. The body portion 54 then contacts the inner surface of the cylindrical portion 62 while the cylindrical portion 55, having a smaller diameter, is spaced from the internal passage walls of the cylindrical portion 62. The relative axial lengths of the body portions 54 and 55 can be adjusted to control the friction that occurs during relative rotation between the centering mechanism 61 and the actuator 52.

The end body portion 56 of the actuator 52 emerges from the centering mechanism 61. This body portion 56 attaches to a planar clamp body 74 by passing through a cylindrical, axially extending bore 75. When the clamp body 74 is attached, the entire mechanism including the actuator 52, spring 57, sleeve 40, centering mechanism 61 and clamp body 74 capture the arms 11 and 12 to provide a unitary device.

Now referring to FIG. 1, the clamp body 74 has a surface 80 that faces the support surfaces 65 and 66. The center claw 43 has first and second elongated toothed surfaces 81 and 82 extending along each side of an elongated slot 83. The teeth are configured to provide an interference that prevents any movement of the center claw 43 that would close any tissue opening. That is, when the clamp body 74 engages the elongated portions 81 and 82 in the transverse orientation shown in FIG. 1, a surgeon can not move the center claw downward in the orientation shown in FIG. 1. However, the center claw 43 will move in the opposite direction without having to manipulate the clamp body 74. Thus, the surgeon need merely pull on the finger grip 50 to increase tissue separation by the center claw 43.

Figure 4:
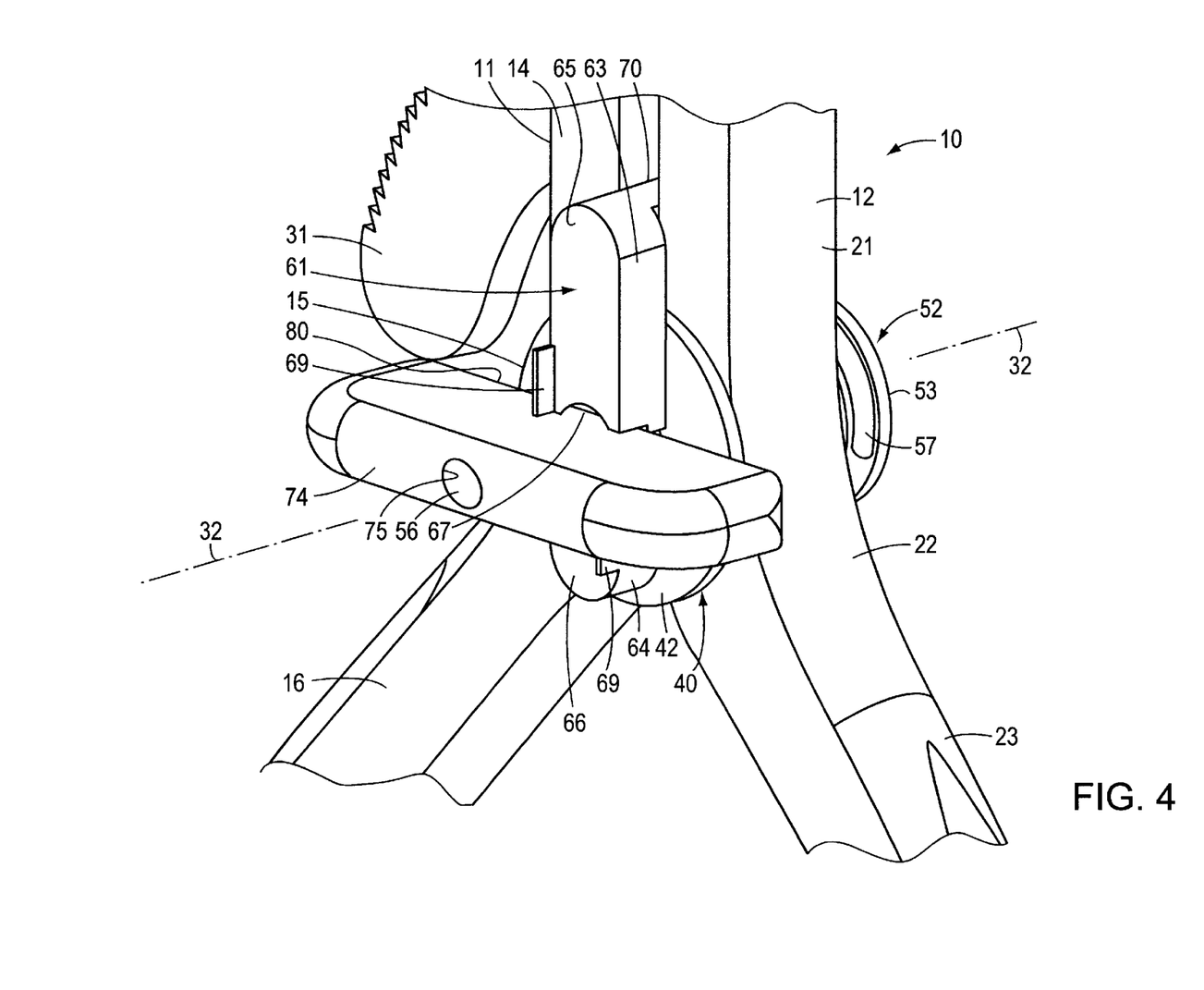
FIG. 4 is an enlarged perspective view a portion of the retractor corresponding to the portion shown in FIG. 3.

Now referring to the use of the retractor 10, FIGS. 3 and 4 depict the clamping mechanism of this invention in a position that would typically exist when the retractor 10 was being used without any center claw. The clamp 74 lies transversely to the centering mechanism so the clamp moves into the cavity 67 under the bias of the compression spring 57 acting against the head 53 of the actuator 52. As previously indicated, all the elements are captured between the actuator head 53 and the clamp 74, so this structure assures that all the retractor elements remain in an appropriate operational relationship.

Now assume that a surgeon wishes to add a center claw 43 to the retractor 10. The surgeon grasps the retractor 10 in one hand and depresses the actuator head 53 thereby compressing the the spring 57 and displacing clamp 74 from the cavity 67. The axial displacement is limited so that the clamp 74 clears the cavity 67, but does not clear the tabs 69.

In this position, the tabs 69 initially limit any rotary motion to a first direction, a counter clock-wise direction as shown in FIG. 4. As the surgeon rotates the clamp 74 in that direction, the surface 80 overlaps the surfaces 65 and 66. The surgeon can release the head 53 at any time after this overlap occurs whereupon the arms 63 and 64 will maintain the axial displacement of the clamp 74. The surgeon then can continue to rotate the clamp 74 until it contacts the tabs 69 moving in the counter clockwise direction whereupon the clamp 74 will be aligned with the centering mechanism 61 as shown in FIG. 5 and the clamp has been moved axially and angularly to a mounting end position.

Figure 5:
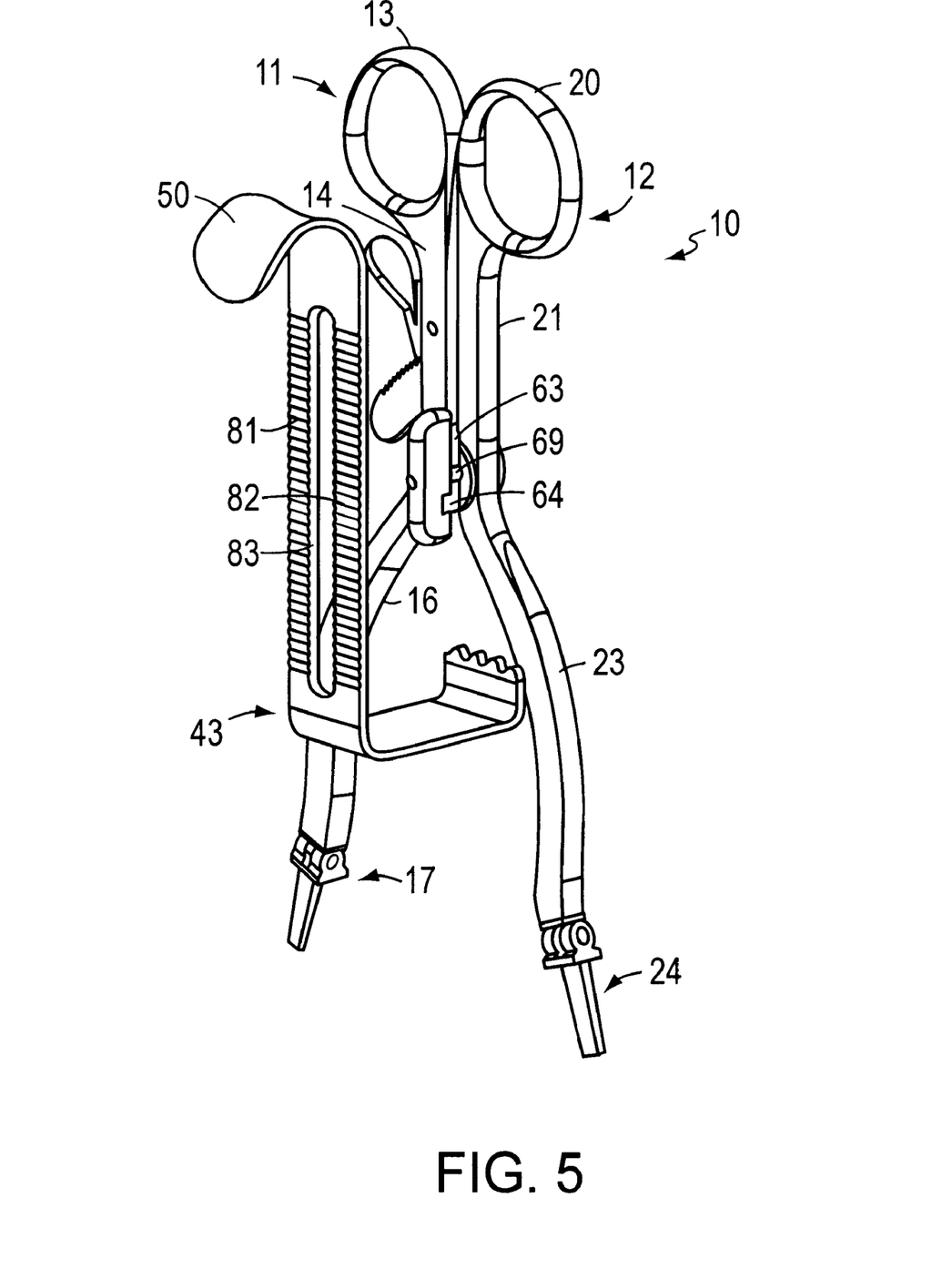
FIG. 5 depicts the retractor of FIG. 1 with the central claw detached and aligned for attachment.

Continuing to refer to FIG. 5, now the surgeon can align the elongated slot 83 of the center claw 43 with the clamp 74 and simply slide the center claw over the clamp 74 and onto the radial body portions 63 and 64. The depth of the radial body portions is selected to be slightly greater than the thickness of the center claw 43. In subsequent operations, the body portions 63 and 64 control the alignment of the center claw 43. As previously indicated, the springs 72 and 73 in FIG. 2 maintain the centering mechanism in a position so that the body portions 63 and 64 always lie along an axis that bifurcates the arms 11 and 12. Consequently, the centering mechanism 61 assures that the center claw 43 lies along that same bifurcating axis notwithstanding the degree of separation of the arms 11 and 12.

After positioning the claw 43, the surgeon can rotate the clamp 74 in a clockwise direction away from the tabs 69 to a clamping end position as shown in FIG. 1. The clamp 74 is again transversely positioned relative to the centering mechanism 61. As it reaches this angular position, the clamp aligns with the cavity 67. The compression spring 57 then drives the actuator head 53 in a direction shown by arrow B until the clamp 74 enters the cavity 67. The axial displacement is limited when the toothed surface 80 of the clamp 74 engages the toothed surfaces 81 and 82 of the center claw 43. In this clamping end position, the body portions 63 and 64 partially overlap the clamp 74. This overlap prevents inadvertent rotation of the clamp 74 during use. That is, a surgeon must make a definite decision to unlock the clamp 74 because the surgeon must displace the clamp 74 both angularly and axially to effect any such unlocking.

As previously indicated, the toothed surfaces 80, 81 and 82 provide a ratchet function. The surgeon can retract the center claw 43 without manipulating the clamp 74. However, the teeth constitute one approach that produces a positive interference between the clamp 74 and center claw 43 that prevents any motion in the opposite direction. Should such displacment be desired, the surgeon can, with one hand, release the clamp 74 by axially moving the actuator 53 a distance that allows the toothed surfaces to clear each other.

Still another mode of operation can occur if the surgeon rotates the clamp 74 to an angular position intermediate the positions shown in FIGS. 1 and 5. As previously indicated, in that position the surfaces 65 and 66 on the centering mechanism will maintain an axial displacement of the clamp 74. With this displacement, the center claw 43 is free to move in either direction because the opposed teeth do not engage. However, in this position, the clamp 74 still overlaps the center claw 43 and continues to capture the center claw 43 to the retractor. The centering mechanism 61 limits the center claw 43 to linear motion over the length of the slot 83.

Figure 6:
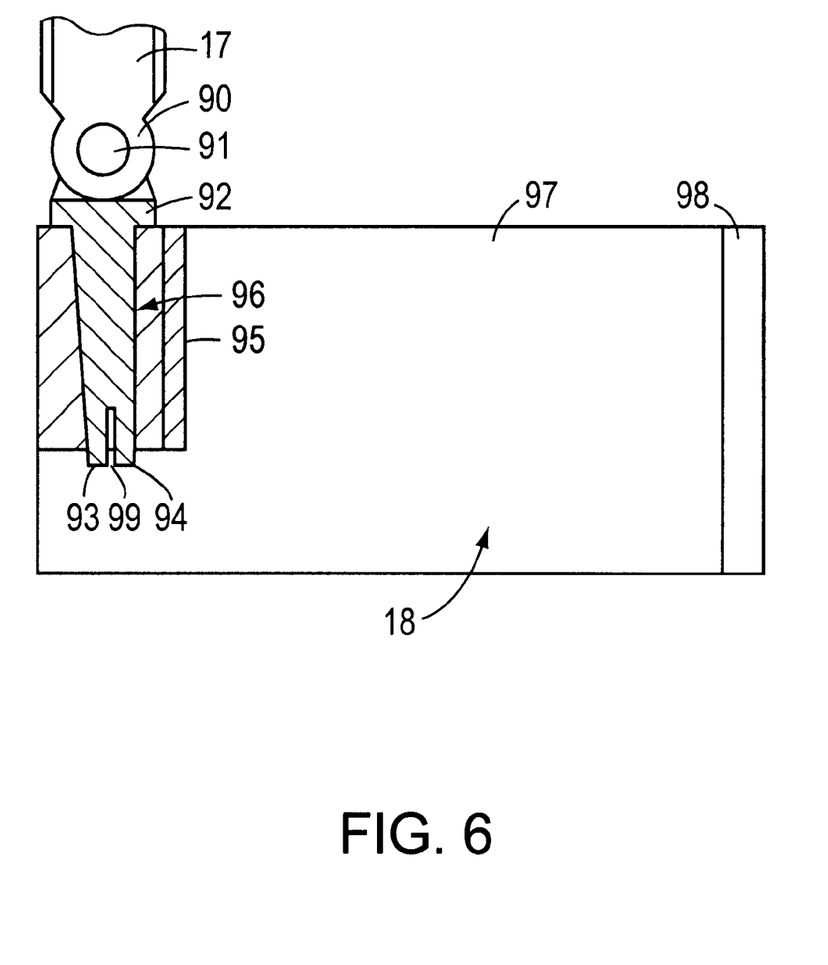
FIG. 6 is a detailed view depicting the attachment of claws to the retractor arms as shown in FIG. 1.

The retractor 10 is further enhanced by providing detachable, hinged claws 18 and 25 as shown in FIG. 1. Looking at the claw coupler 17 and claw 18 in FIGS. 1 and 6, a body portion 90 attaches to the end of the lower arm 16. This body portion carries a tongue that interfits between two tongues to form a pivot 91 for an arm body 92 that terminates with bifurcated arms 93 and 94. In this specific embodiment, the arm body 92 extends in alignment from the lower arm portion 16, but can rotate±900°.

In cross section the bifurcated arm body 92 and arms 93 and 94 taper as they extend from the pivot 91 and have a unique cross section, a D-cross section in this specific embodiment. The claw 18 is formed with a mount 95 having an passage 96. A central portion 97 connects the mount 95 to a claw 98. The passage 96 will have the same cross section as that of the arm body 92. This facilitates the correct orientation of the claw 18 on the coupler 17 upon insertion.

In addition, the passage 96 tapers so that as the arm body 92 enters the passage 96, the arms will compress thereby to provide a tight fit. A further enhancement can be achieved if the arm 94 is narrower than the arm 93 thereby to flex as the arm 93 moves through the passage 96 and if the arm 94 terminates at its free end with an outwardly extending lip 99 positioned to clear the mount 95 when the claw 18 is fully seated. This allows the arm 94 to flex outwardly so that the lip overlaps the end of the mount 95 adjacent the passage 96 and provides a positive detent and locking action that prevents any inadvertent removal of the claw 18 from the coupler 17.

Thus, the retractor 10 shown in FIG. 1 meets the stated objectives of this invention. Specifically, the retractor 10 with the disclosed clamping mechanism allows a surgeon to attach center claw 43 to the retractor 10 readily and, in many situations, with one hand. The retractor is easy to use because the surgeon can adjust the longitudinal position of the center claw with one hand without any need for manipulating the clamping mechanism. The centering mechanism assures that the center claw remains centered whenever the surgeon adjusts the spacing of the retractor arms.

This invention has been disclosed in terms of certain embodiments. It will be apparent that many modifications can be made to the disclosed apparatus without departing from the invention. For example, each of the actuator, centering and clamping members have been shown with specific configurations. The invention has been disclosed in light of a particular form of retractor. The configurations could be modified to meet requirements of other retractor constructions. The positive interference between the clamp and the center claw is accomplished by a one-way ratchet arrangement. Other methods of obtaining such an interference could substituted. Therefore, it is the intent of the appended claims to cover all such variations and modifications as come within the true spirit and scope of this invention.

What is claimed as new and desired to be secured by Letters Patent of the United States is:

1. A tissue retractor adapted for the attachment of an auxiliary element, said tissue retractor comprising:
   A. first and second arms connected to rotate about a pivot axis, each arm including a retractor claw at one end thereof,
   B. a clamp mounted to said first and second arms on the pivot axis for adjustment between first and second positions, said clamp, in its first position, enabling the auxiliary element to be positioned relative to said pivot and, in its second position, clamping the auxiliary element by positive interference with the auxiliary element thereby to prevent relative motion between said clamp and the auxiliary element.

2. A tissue retractor as recited in claim 1 wherein the first and second positions are angularly and axially displaced, said tissue retractor additionally comprising angular and axial motion limits that interact with said clamp.

3. A tissue retractor as recited in claim 2 additionally comprising a ratchet and pawl attached to said first and second arms remotely from the pivot axis, said ratchet and pawl locking said first and second arms in a selected position.

4. A tissue retractor as recited in claim 2 additionally comprising a centering mechanism rotatable about the pivot axis relative to said first and second arms whereby said clamp centers the auxiliary element between said first and second arms.

5. A tissue retractor as recited in claim 2 wherein each said retractor claw includes:
   i) a claw element having a mounting bracket,
   ii) a hinge mounted to the end of a respective one of said first and second arms with a rotatable portion of said hinge engaging said mounting bracket.

6. A tissue retractor as recited in claim 5 wherein said mounting bracket and said rotatable hinge portion have complementary cross sections.

7. A tissue retractor as recited in claim 2 wherein said clamp includes an elongated clamping element for passing through an elongated slot in the auxiliary element and includes a clamping surface for engaging the auxiliary element.

8. A tissue retractor as recited in claim 7 additionally comprising a centering mechanism rotatable about the pivot axis relative to said first and second arms whereby said clamp centers the auxiliary element between said first and second arms.

9. A tissue retractor as recited in claim 8 additionally comprising a ratchet and pawl attached to said first and second arms remotely from the pivot axis, said ratchet and pawl locking said first and second arms in a selected position.

10. A tissue retractor comprising:
    A) first and second arms connected to rotate about a pivot axis, each arm including a retractor claw at one end thereof for engaging tissue,
    B) an auxiliary claw having an elongated intermediate body portion with an elongated slot therethrough,
    C) a central actuator extending through said first and second arms along the pivot axis, and
    D) an elongated clamping member attached to an end of said central actuator, said central actuator and said clamping member being movable axially and angularly relative to said first and second arms between a mounting end position and a clamping end position, said clamping member being aligned with the elongated slot in said auxiliary claw in the mounting end position and being transverse to the elongated slot in the clamping end position.

11. A tissue retractor as recited in claim 10 wherein said central actuator additionally comprises a spring that biases said central actuator and said clamping member to the clamping end position in an axial direction.

12. A tissue retractor as recited in claim 11 wherein each of said auxiliary claw intermediate portion and said clamping member include counterfacing locking surfaces.

13. A tissue retractor as recited in claim 11 wherein each of said auxiliary claw intermediate portion and said clamping member include complementary one-way counterfacing locking surfaces thereby to prevent longitudinal motion of said auxiliary claw in one direction and enable longitudinal motion of said auxiliary claw in another direction when said clamping member is in the clamping end position.

14. A tissue retractor as recited in claim 11 additionally comprising an intermediate member coaxially mounted with said actuator whereby said actuator moves axially relative to said intermediate member, said intermediate member having a support surface facing said clamping member for supporting said clamping member in the mounting end position and having a transverse central slot into which said clamping member passes in the clamping end position.

15. A tissue retractor as recited in claim 14 wherein said intermediate member additionally includes a stop extending from said support surface for limiting the angular rotation of said actuator and clamping member between the mounting and clamping end positions.

16. A tissue retractor as recited in claim 14 additionally comprising a stop extending from said support surface for limiting the angular rotation of said actuator and clamping member between the mounting and clamping end positions, said clamping member being axially displaced in an angular position intermediate the mounting and clamping end positions whereby said auxiliary claw can move relative to said clamping member.

17. A tissue retractor as recited in claim 14 wherein said intermediate member is angularly displaceable with respect to said first and second arms, said retractor additionally comprising first and second springs mounted between the said intermediate member and said first and second arms, respectively whereby said springs position said intermediate member along and axis that bifurcates axes along said first and second arms.

18. A tissue retractor as recited in claim 11 additionally comprising a ratchet and pawl attached to said first and second arms remotely from the pivot axis, said ratchet and pawl locking said first and second arms in a selected position.

19. A tissue retractor as recited in claim 11 wherein each said retractor claw includes:
   i) a claw element having a mounting bracket, and
   ii) a hinge mounted to the end of a respective one of said first and second arms with a rotatable portion of said hinge engaging said mounting bracket, said mounting bracket and said rotatable hinge portion having complementary cross sections.

20. A tissue retractor comprising:
   A) first and second retractor arms each having a grip at a first end and interfitting intermediate portions that define a pivot axis,
   B) a hinged, replaceable claw mechanism at the second end of each arm,
   C) a flanged sleeve mounted through said interfitting intermediate portions in a first direction along the pivot axis, whereby said first and second retractor arms are rotatable about said sleeve,
   D) a centering body having a portion extending into said sleeve in the first direction and being rotatable with respect to said sleeve and to said first and second retractor arms, said centering body having elongated planar support surfaces formed parallel to said flange on said sleeve on opposite sides of the pivot axis,
   E) centering springs between said centering body and each of said first and second retractor arms thereby to center said centering body angularly with said elongated planar support surface lying along an axis intermediate axes through each of said retractor arms,
   F) a spring biased actuator with a transverse portion and a body portion extending through said sleeve and said centering body portion in a second direction along the pivot axis,
   G) an elongated clamp attached to said actuator body portion from the other direction whereby said transverse portion and said clamp are positioned on opposite sides of said interfitting, intermediate portions of said retractor arms, said actuator and said clamp being angularly and axially displaceable between a mounting end position when said clamp is positioned on said support surfaces and a clamping end position when said clamp is rotated to be transverse to said support surfaces,
   H) a center claw having an intermediate portion with an elongated slot and a toothed surface, a claw and a handle portion extending from the opposite ends of said intermediate portion whereby in the mounting end position of said clamp the center claw can be attached to said retractor, whereby in an intermediate position of said clamp the center claw can move in either direction with respect to said clamp and whereby in the clamping end position said clamp and toothed portions of said center claw provide a one-way ratchet to limit motion of said centrer claw toward said handle portions of said first and second arms.

* * * * *